US010952785B2

(12) United States Patent
Zamarripa et al.

(10) Patent No.: US 10,952,785 B2
(45) Date of Patent: Mar. 23, 2021

(54) DEVICE FOR MEDICAL LEAD EXTRACTION (71) Applicant: Medtronic Advanced Energy LLC, Minneapolis, MN (US)

(72) Inventors: Nathan Zamarripa, Kittery Point, ME (US); Mark M. Guirguis, Boston, MA (US); Jessica Sacks, Lynnfield, MA (US); Brian M. Conley, South Berwick, ME (US); Stephen R. Polgar, Taunton, MA (US)

(73) Assignee: MEDTRONIC ADVANCED ENERGY, LLC, Minneapolis, MN (US)

( * ) Notice: Subject to any disclaimer, the term of this patent is extended or adjusted under 35 U.S.C. 154(b) by 545 days.

(21) Appl. No.: 15/662,450

(22) Filed: Jul. 28, 2017

(65) Prior Publication Data
US 2018/0028258 A1    Feb. 1, 2018

Related U.S. Application Data (60) Provisional application No. 62/369,472, filed on Aug. 1, 2016.

(51) Int. Cl.
*A61B 18/12*     (2006.01)
*A61B 18/14*     (2006.01)
(Continued)

(52) U.S. Cl.
CPC ........ *A61B 18/14* (2013.01); *A61B 17/32053* (2013.01); *A61B 17/3468* (2013.01);
(Continued)

(58) Field of Classification Search
CPC .......... A61B 17/32053; A61B 17/3468; A61B 18/14; A61B 18/1492; A61B 2017/22035;
(Continued)

(56) References Cited

U.S. PATENT DOCUMENTS 3,285,773 A    11/1966  Dunning
3,510,343 A     5/1970  Twells et al.
(Continued)

FOREIGN PATENT DOCUMENTS

EP    1903957 B1    12/2011
GB    1465372 A      2/1977
WO    2009046002 A1  9/2009

OTHER PUBLICATIONS

Neuzil et al., "Pacemaker and ICD Lead Extraction with Electrosurgical Dissection Sheaths and Standard Transvenous Extraction Systems: Results of a Randomized Trial," EP Europace, vol. 9, Issue 2, Feb. 2007, pp. 98-104.
(Continued)

*Primary Examiner* — Daniel W Fowler
(74) *Attorney, Agent, or Firm* — Patterson Thuente Pedersen, P.A.

(57) ABSTRACT

An electrosurgical hand piece device is configured to cut tissue with monopolar RF energy to extract a medical lead submersed in fluid. The device includes an electrode surrounded by an electrically insulating coating that can be exposed from a distal edge of the electrode when power is supplied to the device, thereby focusing the energy at the distal edge and enabling tissue to be more easily and safely cut from around the medical lead while in fluid.

19 Claims, 8 Drawing Sheets

(51) Int. Cl.
*A61B 17/3205* (2006.01)
*A61B 17/34* (2006.01)
*A61N 1/05* (2006.01)
*A61B 18/18* (2006.01)
*A61B 17/22* (2006.01)
*A61B 18/00* (2006.01)

(52) U.S. Cl.
CPC ............... *A61B 18/1492* (2013.01); *A61B 2017/22035* (2013.01); *A61B 2018/00357* (2013.01); *A61B 2018/00601* (2013.01); *A61B 2018/1253* (2013.01); *A61B 2018/1861* (2013.01); *A61N 2001/0578* (2013.01)

(58) Field of Classification Search
CPC ........... A61B 2018/00357; A61B 2018/00601; A61B 2018/1253; A61B 2018/1861
See application file for complete search history.

(56) References Cited

U.S. PATENT DOCUMENTS

| | | | |
|---|---|---|---|
| 4,582,056 A | 4/1986 | McCorkle, Jr. | |
| 4,960,419 A * | 10/1990 | Rosenberg | A61B 18/1402 30/296.1 |
| 5,423,806 A | 6/1995 | Dale et al. | |
| 5,573,529 A | 11/1996 | Haak et al. | |
| 5,776,613 A | 7/1998 | Shimatani et al. | |
| 5,779,715 A | 7/1998 | Tu | |
| 5,980,515 A | 11/1999 | Tu | |
| 6,033,402 A | 3/2000 | Tu et al. | |
| 6,071,283 A | 6/2000 | Nardella et al. | |
| 6,135,998 A | 10/2000 | Palanker | |
| 6,176,857 B1 * | 1/2001 | Ashley | A61B 18/08 606/32 |
| 6,183,469 B1 | 2/2001 | Thapliyal et al. | |
| 6,241,692 B1 | 6/2001 | Tu et al. | |
| 6,379,351 B1 | 4/2002 | Thapliyal et al. | |
| 6,419,674 B1 | 7/2002 | Bowser et al. | |
| 6,616,744 B1 | 9/2003 | Sainz et al. | |
| 6,623,437 B2 * | 9/2003 | Hinchliffe | A61B 10/04 600/564 |
| 7,107,105 B2 | 9/2006 | Bjorklund et al. | |
| 8,128,636 B2 | 3/2012 | Lui et al. | |
| 8,192,430 B2 | 6/2012 | Goode et al. | |
| 8,428,747 B2 | 4/2013 | Coe et al. | |
| 8,439,910 B2 | 5/2013 | Greep et al. | |
| 8,480,696 B2 * | 7/2013 | Clague | A61B 17/00008 606/159 |
| 8,632,558 B2 | 1/2014 | Chin et al. | |
| 9,023,040 B2 | 5/2015 | Bloom et al. | |
| 9,028,520 B2 | 5/2015 | Taylor et al. | |
| 9,149,290 B2 | 10/2015 | Goode et al. | |
| 9,155,878 B2 | 10/2015 | Goode et al. | |
| 2001/0012936 A1 * | 8/2001 | Heim | A61B 18/14 606/45 |
| 2003/0014047 A1 * | 1/2003 | Woloszko | A61B 18/1485 606/41 |
| 2003/0125732 A1 * | 7/2003 | Goble | A61B 18/14 606/48 |
| 2005/0070894 A1 * | 3/2005 | McClurken | A61B 18/1492 606/48 |
| 2005/0149096 A1 | 7/2005 | Hilal et al. | |
| 2008/0027428 A1 * | 1/2008 | Palanker | A61B 18/1402 606/45 |
| 2010/0009203 A1 | 1/2010 | Nageno et al. | |
| 2010/0106153 A1 * | 4/2010 | West, Jr. | A61B 18/1482 606/33 |
| 2010/0129726 A1 | 5/2010 | Tanida et al. | |
| 2010/0198229 A1 | 8/2010 | Olomutzki et al. | |
| 2010/0222787 A1 | 9/2010 | Goode et al. | |
| 2012/0171420 A1 | 7/2012 | Molins et al. | |
| 2012/0191084 A1 | 7/2012 | Davison et al. | |
| 2012/0282407 A1 | 11/2012 | Singh et al. | |
| 2013/0226176 A1 * | 8/2013 | Kuehner | A61B 17/3203 606/45 |
| 2014/0031800 A1 | 1/2014 | Oren et al. | |
| 2014/0276696 A1 | 9/2014 | Schneider | |
| 2014/0276926 A1 | 9/2014 | Hendrick | |
| 2014/0296897 A1 | 10/2014 | Sotak et al. | |
| 2015/0031524 A1 | 1/2015 | Takayama | |
| 2016/0022302 A1 | 1/2016 | Olomutzki et al. | |
| 2019/0185370 A1 | 6/2019 | Cheng et al. | |
| 2019/0192213 A1 | 6/2019 | Cheng et al. | |

OTHER PUBLICATIONS

Okamoto et al., "Extraction of Recalled Riata Leads," The Journal of Innovations in Cardiac Rhythm Management, 4, 2013, pp. 1305-1314.

Perfecta Electrosurgical Dissection System, Cook Vascular Incorporated, Jan. 2013, pp. 1-144.

* cited by examiner

DEVICE FOR MEDICAL LEAD EXTRACTION

PRIORITY

This application claims the benefit of and priority to U.S. Provisional Application No. 62/369,472, filed Aug. 1, 2016.

TECHNICAL FIELD

The present invention relates to a medical lead extraction device, and in particular, an electrosurgical hand piece configured to cut tissue with monopolar radiofrequency ("RF") energy to extract a medical lead submersed in fluid.

BACKGROUND

Cardiac pacemakers and implantable cardioverter defibrillators (ICDs) are devices implanted within patients' bodies to treat various cardiac conditions. These devices include a power source that sends electrical signals down a cardiac lead that extends from the power source to a patient's heart. The cardiac leads can be epicardial leads, which are leads with electrodes attached to the outside of the heart, or endocardial leads, which are leads that are inserted through a vein and guided into a chamber of the heart through the vein.

Although implanted cardiac leads typically have a useful life of many years, at some point leads may become inoperative, another type of lead may be needed or the corresponding pacemaker or ICD may be removed. Although cardiac leads can be left in the heart, doing so can lead to serious medical complications for the patient. It is therefore often desirable to surgically remove such leads. In addition, there are circumstances that make removal of the lead a medical necessity, such as infection or vein obstruction.

Complicating removal of an endocardial lead extending through a patient's vein is the fact that over time, the lead tends to become encapsulated against the wall of the vein by fibrotic tissue. The fibrotic tissue can make separation and removal of the lead from the vein difficult, and severe damage can be caused removing the lead, including possible dissection or perforation of the vein.

A number of methods and devices have been developed for removing cardiac leads encapsulated by fibrotic tissue from veins of patients. One exemplary device is disclosed in U.S. Pat. No. 5,980,515 to Tu. This device includes a cylindrical, non-conductive delivery catheter with a conductive electrode at its distal end. A conducting wire connected to an external radiofrequency (RF) energy source is secured to the electrode to deliver RF energy to the electrode. In use, the electrode and delivery catheter are advanced over an implanted cardiac lead. The RF energy source is activated and a sharp edge of the electrode is advanced into the fibrotic tissue encapsulating the lead, such that the fibrotic tissue is removed by a combination of the RF energy and mechanical cutting by the sharp edge of the electrode. As the fibrotic tissue is cut away, the cardiac lead can be removed from the vein.

Studies have found that devices employing bipolar RF energy can cause harm to patients including in some cases death and therefore monopolar RF energy is generally safer and preferred. Current monopolar RF-based lead extraction devices, however, face challenges for use in in vivo fluid environments such as when immersed in blood within a vein. Specifically, it has been a challenge for electrodes to fire or deliver sufficient RF energy to dissect tissue when completely submersed in a fluid such as blood. This is significant because modern RF electrosurgery technology leverages plasma generation by ionizing air to cause tissue dissection. When an RF electrode is completely submersed in blood as opposed to air, current density drops because the exposed surface of the electrode is in contact with the blood, which is a conductive medium, resulting in a lower impedance around the electrode. Moreover, because of the lower impedance in liquids, creating plasma in such an environment is challenging. If plasma is not created, then RF dissection/ablation becomes ineffective and the device is unable to dissect the tissue to remove the lead.

SUMMARY

The present invention advantageously provides an electrosurgical hand piece device configured to cut tissue with monopolar RF energy to extract a medical lead submersed in fluid. The device includes an electrode surrounding by an electrically insulating coating that can be exposed from a distal edge of the electrode when power is supplied to the device, thereby focusing the energy at the distal edge and enabling tissue to be more easily and safely cut from around the medical lead while in fluid.

In an exemplary embodiment, a medical lead extraction system includes a hollow flexible elongate catheter, a handle attached to a proximal end of the catheter, and a hollow electrode attached to a distal end of the catheter. The hollow electrode can have a distal cutting edge and be configured to be advanced over a cardiac lead disposed within a blood vessel of a patient. A conductor can extend along the catheter and attach to the hollow electrode to transmit electrical energy from a power source to the hollow electrode. An electrically insulating coating can surround the hollow electrode with the coating configured to degrade from and expose the distal cutting edge of the hollow electrode when the electrical energy is transmitted to the hollow electrode. This enables the distal cutting edge to transmit the electrical energy to aid in dissecting tissue to remove the cardiac lead.

In an exemplary embodiment, a method of removing a cardiac lead from within a blood vessel of a patient can include inserting a hollow flexible elongate catheter into a blood vessel of a patient. The catheter can include a hollow electrode attached to a distal end of the catheter that is advanced over a medical lead disposed in the blood vessel to contact a distal cutting edge of the hollow electrode with tissue surrounding the medical lead. Electrical energy can be provided to the hollow electrode that can cause a coating surrounding the hollow electrode to degrade from and expose the distal cutting edge of the hollow electrode. The tissue surrounding the medical lead can then be removed with the distal cutting edge of the hollow electrode.

Various embodiments of systems, devices and methods have been described herein. These embodiments are given only by way of example and are not intended to limit the scope of the present invention. It should be appreciated, moreover, that the various features of the embodiments that have been described may be combined in various ways to produce numerous additional embodiments. Moreover, while various materials, dimensions, shapes, implantation locations, etc. have been described for use with disclosed embodiments, others besides those disclosed may be utilized without exceeding the scope of the invention.

BRIEF DESCRIPTION OF THE DRAWINGS

A more complete understanding of the present invention, and the attendant advantages and features thereof, will be more readily obtained by reference to the following detailed description when considered in conjunction with the accompanying drawings wherein.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

Figure 1:
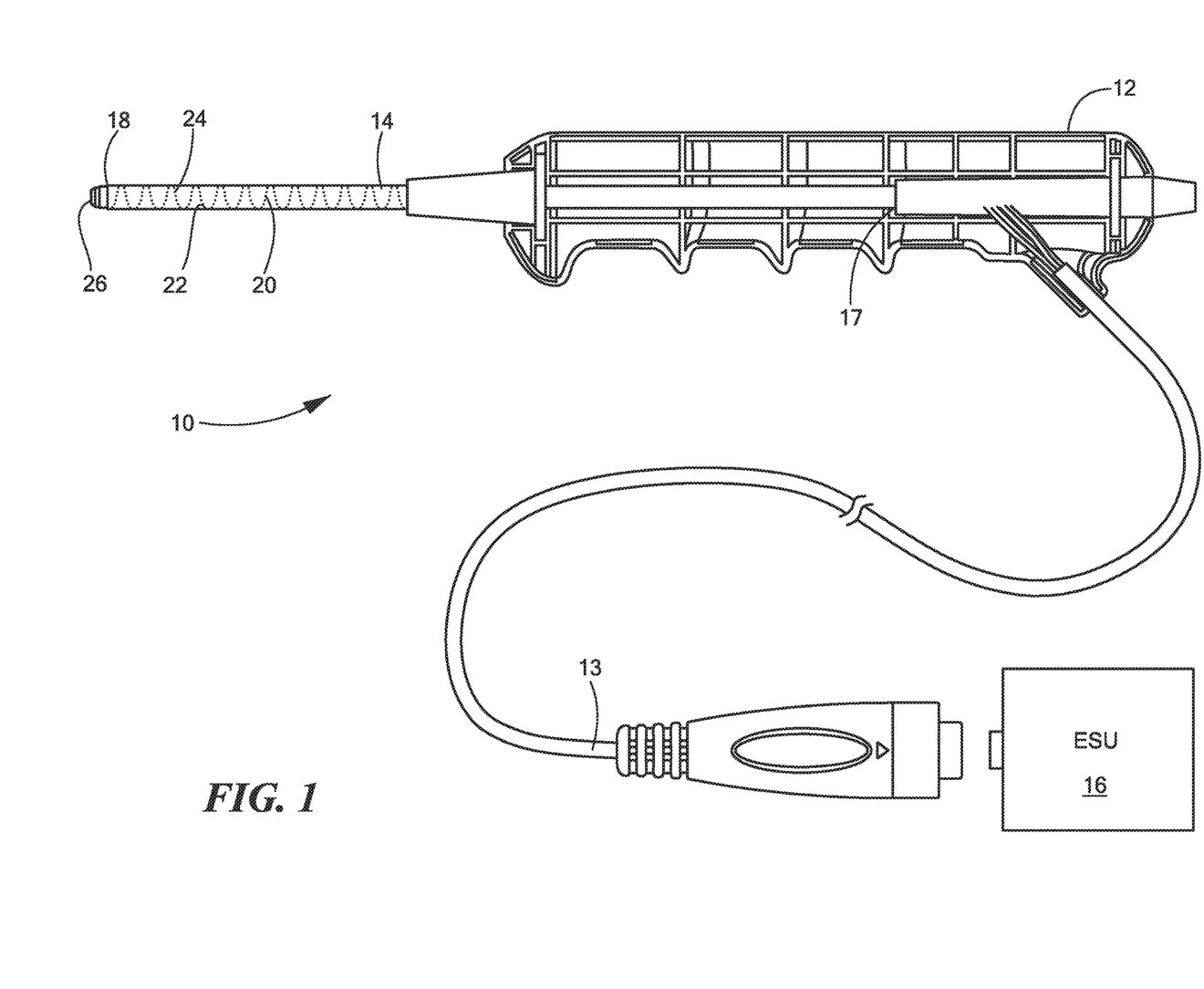
FIG. 1 is a side cross-sectional view of an exemplary electrosurgical medical device constructed in accordance with the principles of the present application.

Referring now to the drawings in which like reference designators refer to like elements, FIG. 1 depicts an exemplary electrosurgical medical device 10 constructed in accordance with the principles of the present application. The medical device 10 can include a hand piece including a handle 12 with a connector 13 extending proximally therefrom for connection to an electrosurgical unit 16 configured to generate and provide monopolar radiofrequency (RF) energy to the device 10. The device 10 can include one or more finger switch buttons (not shown) for activating the device 10 and can include an actuator for providing selective torque to a distal portion of the device 10. Moreover, a return electrode (not shown), e.g. a back plate, can also be included to provide a pathway for monopolar ablation from the device 10 to a patient.

An elongate flexible catheter can extend from the distal end of the handle 12. The elongate flexible catheter 14 can define a proximal end 17 and a distal end 18 and at least one lumen 20 there through. In an exemplary configuration, the elongate catheter 14 is a non-conductive catheter at least partially composed of a flexible material, such as nylon or Pebax®. The catheter 14 can further include a lubricious liner 22 which coats the inner surface of the catheter 14 to reduce friction as the catheter 14 is advanced over the lead to provide smoother lead removal with improved tactile feel. In one configuration, the elongate catheter 14 includes an electrically insulating material within the inner diameter of the lumen 20 and can include heat shrink tubing or other insulative coating or material on its exterior surface to further discourage or prevent the transmission of energy out of the catheter. The elongate catheter 14 can in various embodiments be a catheter having a size between, for example, 8 Fr. and 16 Fr., can have varying (e.g., increasing) flexibility along its major longitudinal axis from its proximal end 17 to its distal end 18, and can have one or more inflexible or malleable sections along such axis so as to assist the user in inserting, navigating or advancing catheter 14 into position.

A conductor 24 configured to provide power from the electrosurgical unit 16 to the distal end 18 of the elongate catheter 14 can be disposed in or within catheter 14, e.g., within lumen 20. In one configuration, the conductor 24 can be configured as a wire coiled along the length of the elongate catheter 14 such that the conductor 24 is in contact with the inner diameter of the elongate catheter 14 from the proximal end 17 to the distal end 18 of the elongate catheter 14. In another configuration, the conductor 24 can be embedded within the wall of the elongate catheter 14. In various embodiments, the catheter 14 can have non-preferential bending characteristics such that elongate catheter 14 does not more easily bend in a particular direction or along a particular plane, but instead can easily bend in multiple directions. Due to the ability to easily bend in multiple directions, a configuration that does not have preferential bending enables the elongate catheter 14 to be advanced within the body around tortuous areas with greater control and less risk of unwanted tissue damage. In an exemplary configuration, the conductor 24 is surrounded by a non-conductive coating or structure (e.g., a non-conductive braid, which may be flat or round), that insulates the conductor 24 from the remainder of the elongate catheter 14 and reduces capacitive leakage. Use of a non-conductive structure around the conductor extending along the catheter is significant because without such a structure the conductor would case the catheter to become capacitively coupled to the body, causing significant leaking of the RF energy along the catheter and leading to lower power at the electrode edge.

Figure 2:
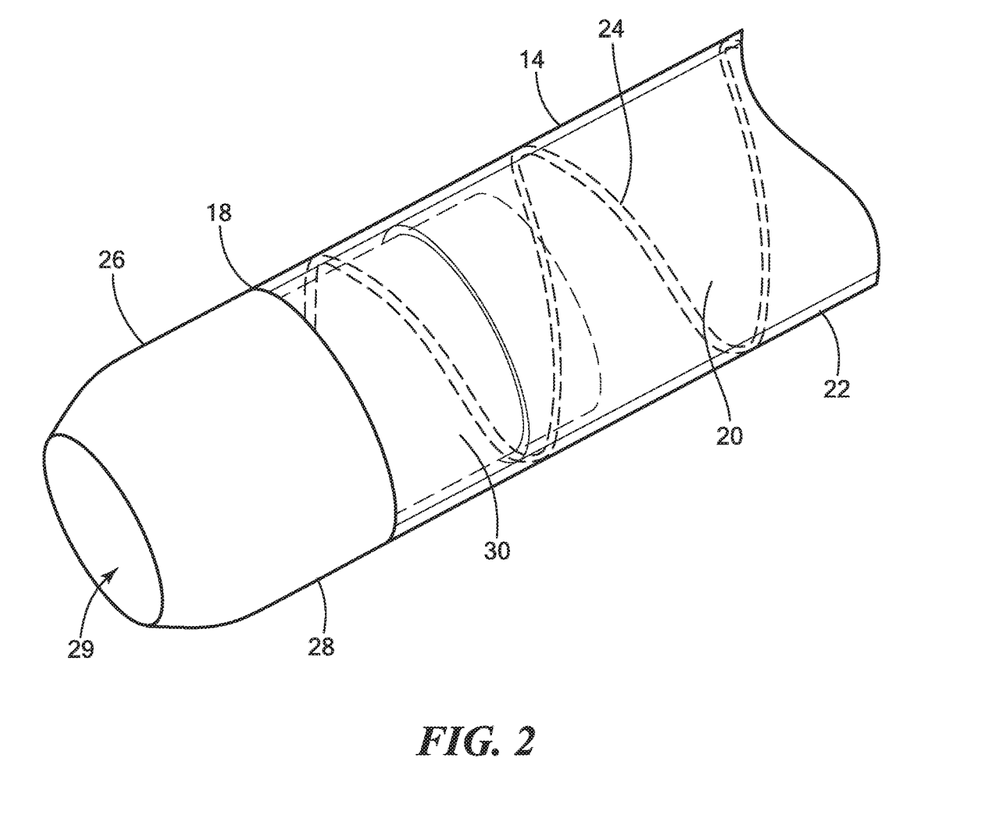
FIG. 2 is a partial side view of the medical device of FIG. 1.
Figure 4:
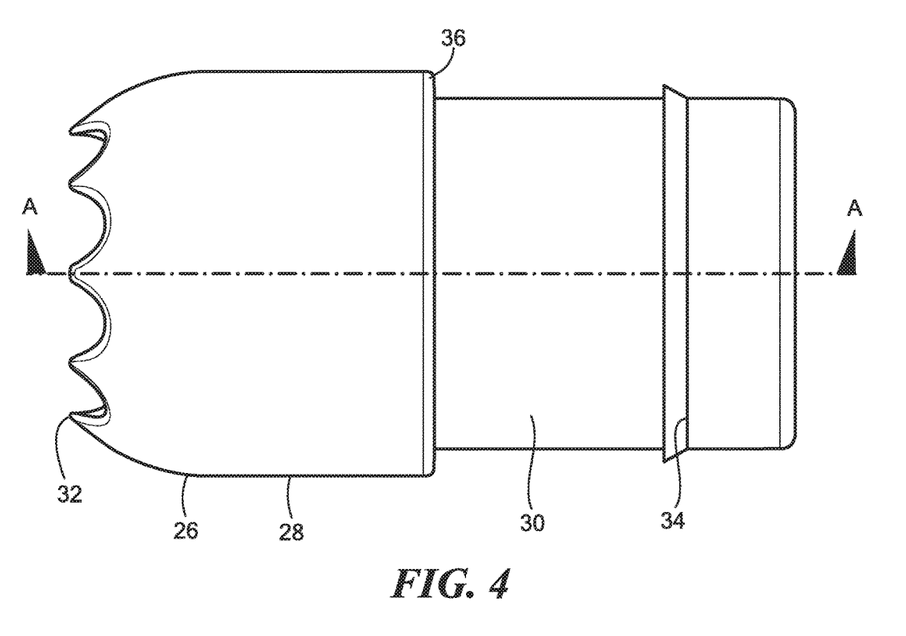
FIG. 4 is a partial side view of another embodiment of an electrosurgical medical device.

An electrode 26 configured to deliver monopolar (RF) energy to a target tissue region can be coupled to the distal end 18 of the elongate catheter 14. In an exemplary configuration shown in FIG. 2, the electrode 26 includes a first portion 28 extending away from the distal end 18 of the elongate catheter 14 having a first outer diameter and a second portion 30 extending into the elongate catheter 14 having a second outer diameter less than the first outer diameter. This enables the conductor 24 to make contact with the electrode 26, and transmit energy thereto, with a conductive contact (e.g., a solder joint) positioned within the catheter, preferably providing a liquid tight, insulated connection. In one configuration, the first portion 28 of the electrode 26 is a hollow metallic substantially cylindrical element with an opening 29 sized to receive a medical lead. The second portion 30 of the electrode can also be a substantially cylindrical, hollow, metallic element that likewise is sized to receive the lead. In one configuration the first portion 28 includes a cutting edge 32 that is sharpened (e.g., serrated as shown in FIG. 4) at its distal end to enhance the ability of the edge 32 to cut calcified tissue. In other configurations, the distal end of the first portion 28 has a smooth cylindrically uniform cutting edge that is thinly sharpened. In operation, such a uniform cutting edge is generally sufficient to remove most tissue adhesions by advancing the electrode without rotation. For more challenging procedures involving calcified tissue, a non-uniform cutting edge (e.g., a serrated edge) can be used to employ mechanical cutting by rotating the serrated edge in addition to the RF energy. In various embodiments, the cutting edge 32 can be a continuous edge extending circumferentially around the distal edge of the electrode. In the context of the cylindrical electrode depicted, such a continuous, circumferential edge is generally circular. However, the cutting edge can have various other geometrical configurations, such as, for example, oval, square, etc.

Figure 5:
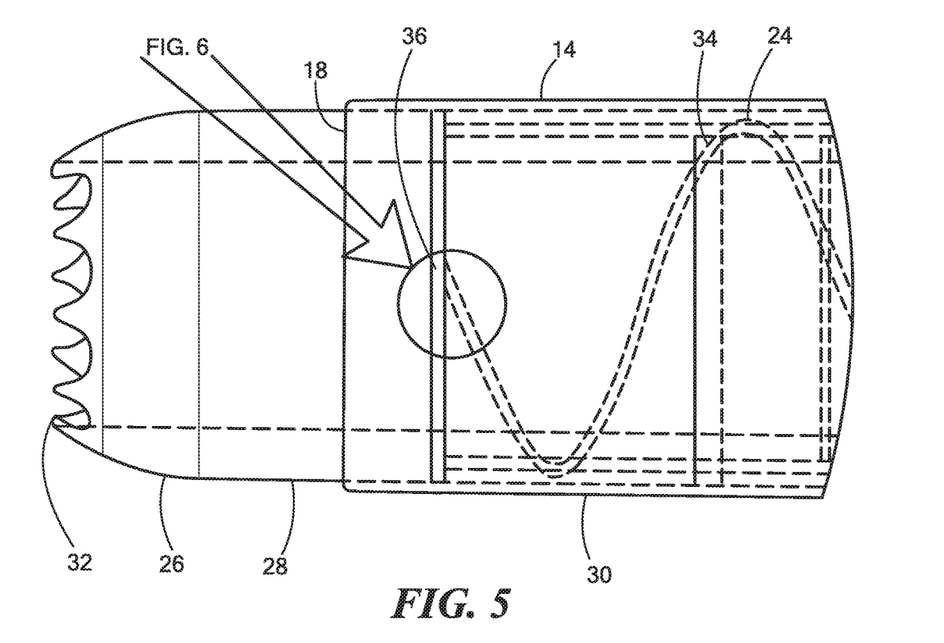
FIG. 5 is a partial side cross-sectional view of the medical device of FIG. 4.
Figure 6:
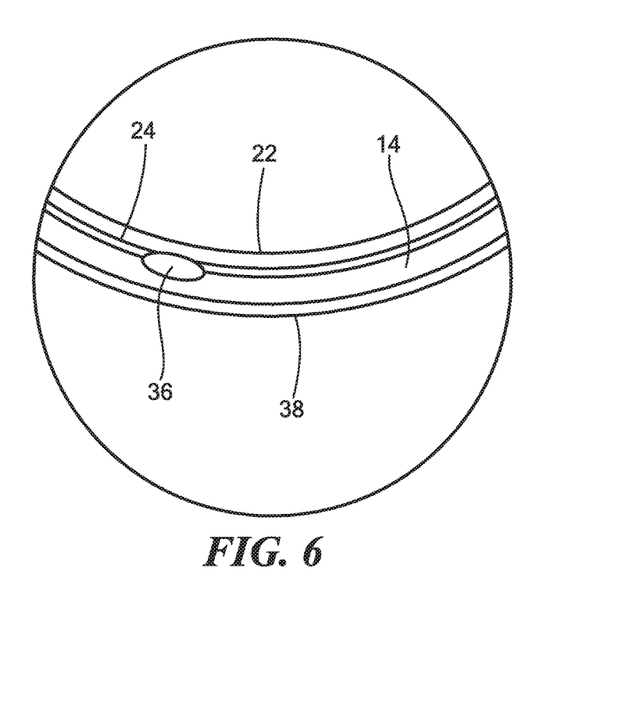
FIG. 6 is a zoomed in view of a portion of the medical device of FIG. 5.

Referring to FIGS. 4-6, the electrode 26 can include a barb 34 or other projecting portion extending outwardly from the second portion 30 of the electrode 26. The barb 34 can be shaped to extend circumferentially around the electrode 26 and can be configured to function as a coupling point of the elongate catheter 14 to the electrode 26. In one configuration, the barb 34 is press fit into the catheter 14 such that the barb 34 engages and captures the interior of the catheter 14 to hold the electrode 26 in place relative to the catheter 14. In some embodiments, a heat shrink tubing can then be applied to the exterior of the catheter 14 adjacent the location of the barb 34 to further retain the electrode 26 therein. The barb 34 can if desired be formed of a conductive material. In one configuration, the barb 34 can provide a welding site at which the conductor 24 is coupled to the electrode 26. In other configurations, the conductor 24 can be welded to a welding site 36 elsewhere on the electrode 26. For example, the welding site 36 can in one configuration be approximately 0.015" in diameter at a location distal to the barb 34 and proximal to the distal end 18 of the catheter 14, as shown in, for example, FIG. 5. In other configurations, the welding site 36 can be positioned anywhere between the barb 34 and the transition between the first portion 28 of the electrode 26 and the second portion 30 of the electrode 26. The welding site 36 can provide a single connection at which electrical energy is transferred from the conductor 24 to the electrode 26. So long as the welding site is suitably positioned within the catheter 14, it can be insulated from the exterior conductive blood surrounding the device. The welding site 36 can be covered with an insulator such as a heat shrink 38 to minimize leakage conductance.

In one configuration, the electrode 26 is coated with an insulative material such as a ceramic or glass enamel coating that insulates substantially covered portions of the electrode 26 from transmitting RF energy. As shown in Section A-A and Detail B of FIG. 3, the entirety of the electrode 26 can initially be coated. This can be done by, for example, dipping the electrode 26 in a suitable dielectric coating material. Suitable dielectric coating materials will be insulative and capable of withstanding high temperatures. Suitable dielectric coating materials desirably also will be capable of bonding to the electrode (which may for example be made from a material such as stainless steel, tungsten, molybdenum, tantalum, titanium, etc.). In addition, suitable dielectric coating materials desirably will have a viscosity such that when the coating cures or otherwise hardens on the electrode, the coating will provide a thin layer of coating in areas where the radius of curvature of the electrode is small (e.g., at the distal cutting edge of the electrode as will be described in more detail below). In certain exemplary embodiments, the insulative material is a ceramic or glass enamel coating made from one or more inorganic oxides such as $K_2O$, $Na_2O$, $ZnO$, $MgO$, $CaO$, $SrO$, $BaO$, $Al_2O_3$, $SiO_2$, $B_2O_3$, $La_2O_3$, $MnO_2$, and $CoO$. Additional exemplary coatings for the electrode 26 are disclosed in U.S. Pat. Nos. 7,458,972, 7,736,361, and 8,211,105, and U.S. Patent Publication No. 2010/0069904, the entirety of which are expressly incorporated by reference herein. In further embodiments, the insulative material need not be a ceramic or glass enamel coating, but can be formed of any other material capable of insulating the electrode body from transmitting energy and withstanding the power transmitted by and the heat produced when operating the device.

Figure 3:
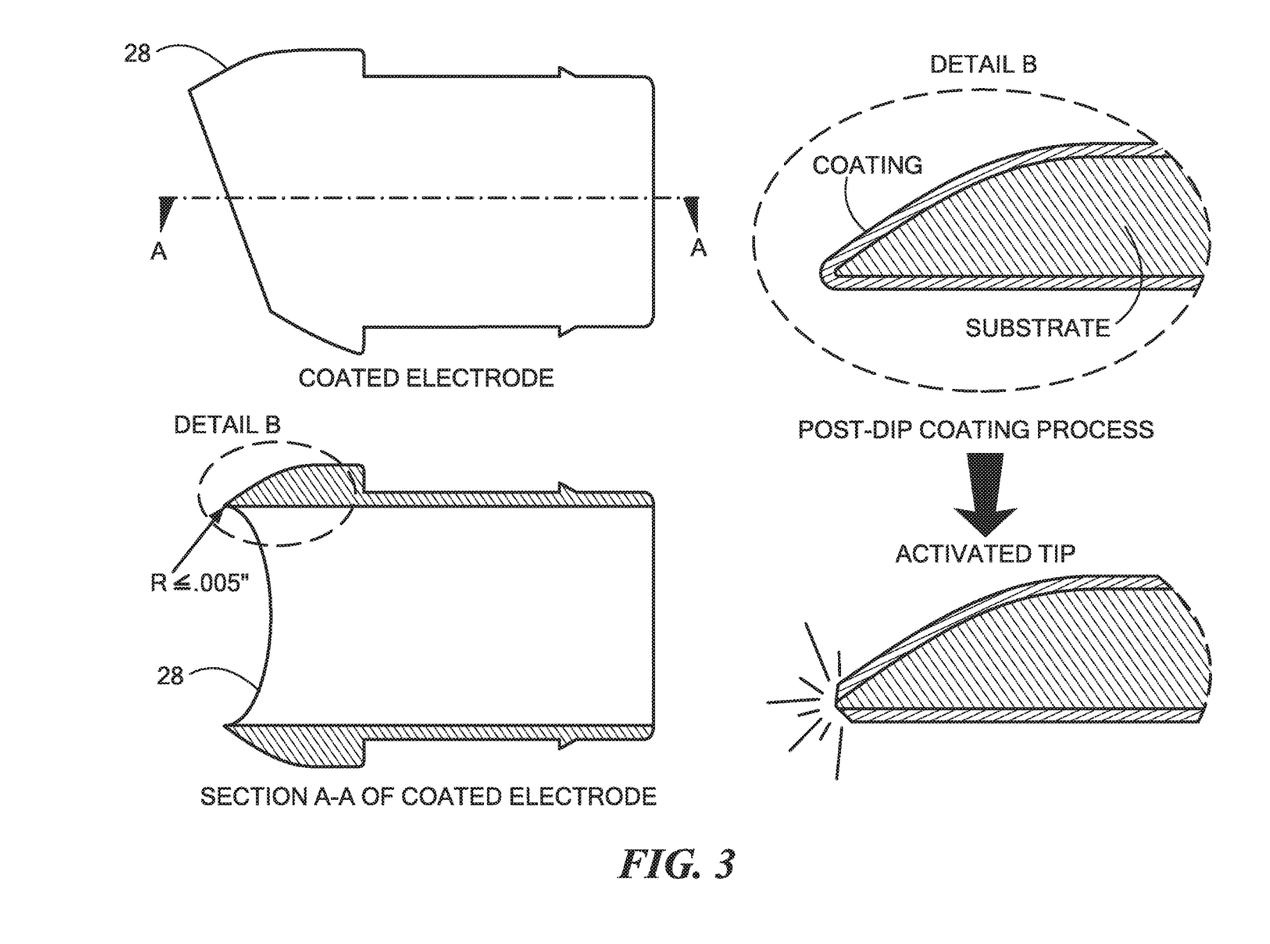
FIG. 3 is a zoomed in view of the electrode tip of FIG. 2 showing an example of a coating process.

As can be seen in Detail B of FIG. 3, the wall of the first portion 28 of the electrode 26 can taper in width as the first portion 28 extends distally from the distal end 18 of the elongate catheter 14 and the first portion 28 of the electrode 26 can also have a decreasing radius of curvature. Due to the decreasing radius of curvature of the electrode 26 as it extends distally, a smaller thickness of the coating material is deposited on the surface of the electrode 26 toward the distal end 18 of the electrode 26, including the cutting edge 32. In various embodiments, a Teflon® or other non-stick coating can be applied over the coating on the exterior of the electrode 26.

When the device 10 is initially activated, the energy provided by the RF power source can cause, in various embodiments, the thinner layer of coating at the cutting edge 32 to degrade. Because the coating is thicker around the cylindrical body of the electrode 26, the coating generally will not degrade from other portions of the electrode. Therefore, the RF energy transmitted by the electrode will be focused only at its cutting edge 32. Limiting the active electrode surface area by use of the coating (e.g., the exposed metal) in this manner results in higher impedance and higher current density at the distal, cutting end of the electrode 26 that better facilitates the generation of plasma when the electrode 26 is disposed in a conductive medium such as blood as opposed to non-coated cylindrical electrodes, which were found to not generate sufficient plasma for tissue dissection. In addition, confining the generation of plasma to this smaller surface area lowers the operating temperature of the electrode such that less power is required to create plasma. In some embodiments, the device 10 can be activated following insertion into the region of the body in which it is being used, e.g., within a vein, but prior to contacting the tissue to be dissected. In other embodiments, the device 10 can be activated at the time resistance in the body is encountered in the form of the tissue to be dissected.

In one configuration, when the device is activated with as little as 3 W of power delivered to the electrode 26 in an aqueous environment such as blood, the coating may degrade from the surface of the cutting edge 32 of the electrode 26 due to the thinness of the coating at that location, for example, when the edge radius on the electrode 26 is less than 0.005". Depending on the particular coating, the coating may, for example, degrade when the temperature of the electrode reaches between 500-800° Celsius for an edge radius less than 0.005". In other configurations, the coating may be etched, grinded, or otherwise mechanically removed from the distal end of the electrode 26 following the coating process.

Figure 8A:
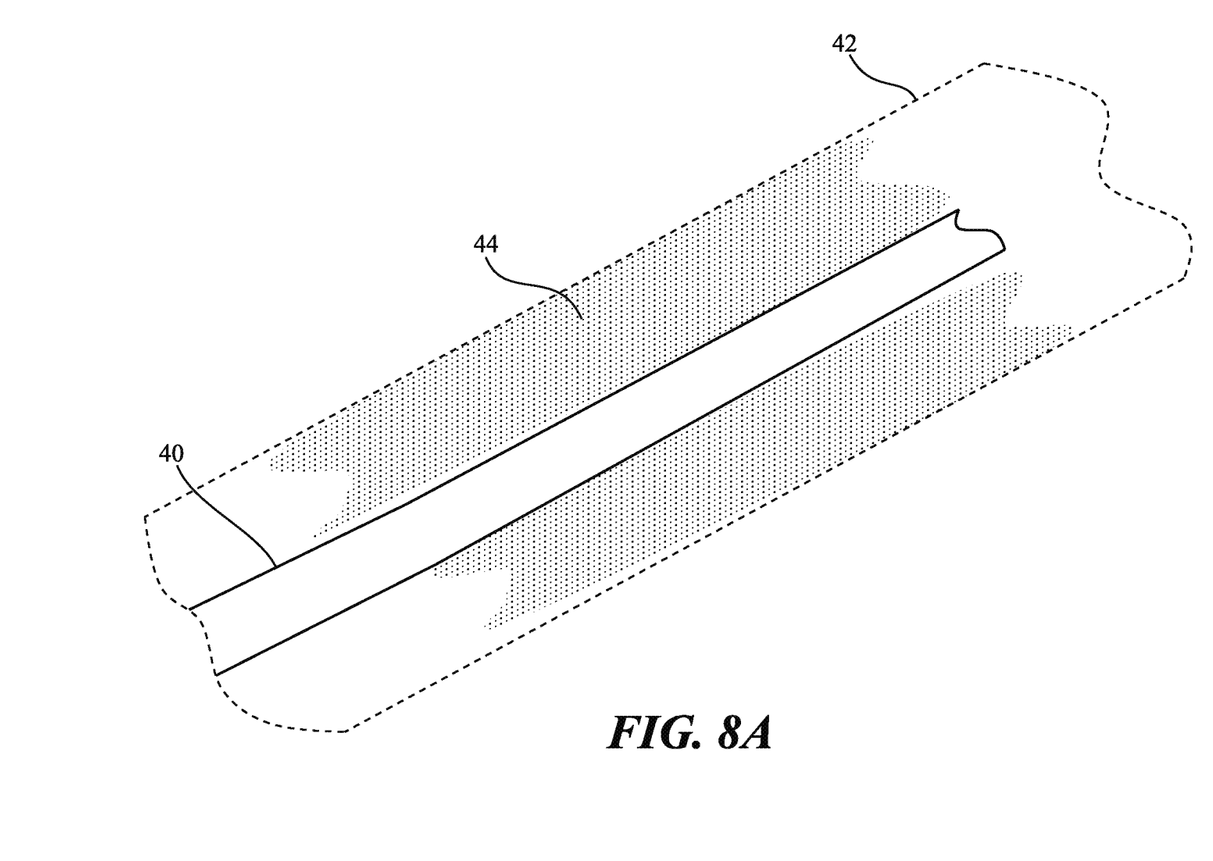
FIGS. 8A-8B depicts an exemplary electrosurgical medical device constructed in accordance with the principles of the present application in use to remove a medical lead from a patient.
Figure 8B:
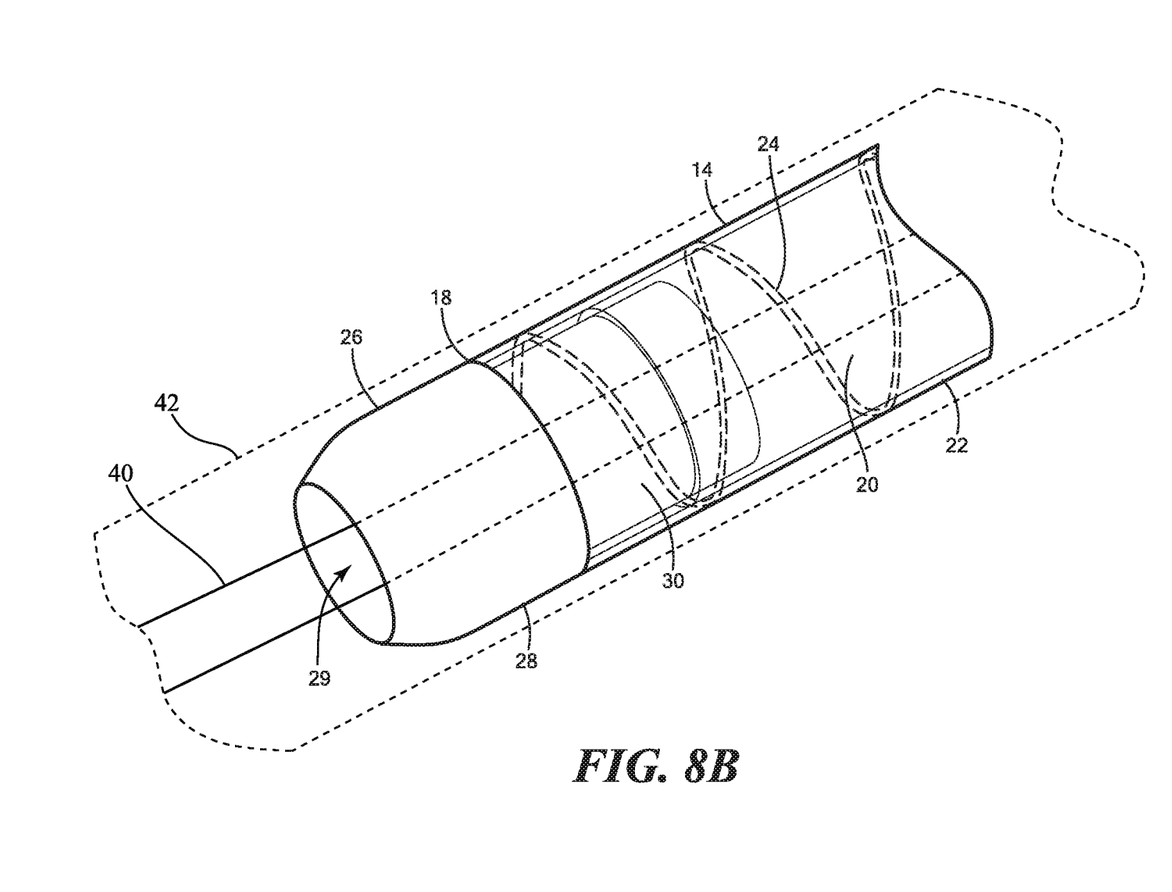

In an exemplary use of the device 10, the reduced capacitance leakage and higher current density at the distal end of the electrode 26 provided by coating a cylindrical electrode with the distal cutting end exposed, or with a thin degradable coating, can facilitate the generation of plasma when the electrode 26 is disposed in a conductive medium such as blood, enhancing the ability of the device 10 to cut tissue and remove a medical lead without damaging surrounding tissue. In a particular application shown in FIGS. 8A-8B, the opening 29 in the electrode 26 may be advanced over a medical lead 40, for example an ICD lead or CRT device lead previously disconnected from the device and extending through a blood vessel 42 of a patient and coupled to the heart in, for example, the right ventricle. As the electrode 26 is advanced over the lead 40, power provided by the RF power source enables the electrode 26 to generate plasma and cut tissue 44, such as, for example, scar tissue, fibrous tissue, and calcium surrounding the lead 40 with the cutting edge 32. Although primarily described herein as being used to remove leads from within blood vessels of a patient, it should be noted that lead removal devices according to the present application could also be used to remove leads from other areas of a patient. For example, the devices described herein could also be used to remove leads placed in the extravascular sub-sternal space (sub-sternal leads).

An exemplary waveform of the energy used for generating plasma with the device 10 in an aqueous environment is a low voltage and constant duty cycle waveform, for example, a pure CUT duty cycle sinusoidal waveform that is always on when activated. This waveform has been tested on a porcine model at various key anatomical locations including the jugular vein, the superior vena cava, the right atrium and the apex of the heart (up to 20 W and 600V) and did not introduce any adverse physiological side effects. In one embodiment, the frequency of the waveform is 470 kHz. The waveform has proven effective to enable the device to dissect soft tissue at 10 W or greater power. A low voltage, constant duty cycle waveform is desirable because waveforms with high peak voltage create the potential for arcing through the lead and conducting currently directly to the myocardium where the lead is fixed. Also, waveforms with a low duty cycle may result in power being delivered on a low carrier frequency (e.g., 300 Hz) which can cause cardiac fibrillation. Another exemplary waveform can be used with monopolar Transcollation® technology, which uses RF energy, with the waveform having a low impedance power curve at, for example, 50 W to 90 W. Optionally, saline may be added to the system. The monopolar Transcollation waveform has also been tested in-vivo on a sheep model at between 50-90 W. Various electrosurgical units 16 can be utilized to generate and provide the desired voltage and waveform to the device 10. Example electrosurgical generators include the Medtronic AEX generator or the Medtronic Pulsar generator available from Medtronic, Inc. of Minneapolis, Minn. and the Bovie generator available from Bovie Medical Corporation of Clearwater, Fla.

In an exemplary embodiment, an electrosurgical medical device 10 includes an elongate catheter 14 having a proximal end 17, a distal end 18, and at least one lumen 20 there through. The catheter 14 is sized to receive a medical lead within the lumen 20. A lubricious liner 22 can coat the interior of the elongate catheter 14. A hollow cylindrical electrode 26 is coupled to the distal end 18 of the elongate catheter 14, the electrode 26 including a first portion 28 extending distally away from the distal end 18 of the catheter 14 and a second portion 30 disposed within the lumen 20 of the catheter 14. The electrode 26 is configured to deliver monopolar RF energy configured to cut tissue. The first portion 28 of the electrode 26 can be tapered in thickness as it extends distally away from the catheter 14. The electrode 26 can initially be entirely coated or otherwise covered with a dielectric material configured to prevent the transmission of monopolar radiofrequency energy at a predetermined coating thickness of the dielectric material. A coiled conductor 24 is disposed within the elongate catheter 14 and coupled to the second portion 30 of the electrode 26 at a coupling location proximal to the distal end 18 of the catheter 14. The coupling location can include an insulating material covering the coiled conductor 24 at the coupling location. When energy is provided to the electrode 26 from an RF power source via the conductor 24, the energy can cause the dielectric coating material to degrade from a cutting edge 32 at the distal end of the electrode 26. This provides reduced capacitance leakage and higher current density at the distal end of the electrode for cutting tissue to remove a lead.

In order to remove a given lead, the opening 29 in the electrode 26 has to be advanced over the lead. If the opening is not advanced over the lead, such as because the lead is too large for the opening or the opening is not properly aligned with the lead, the device will push against the lead and cause the lead and insulation to bunch together rather than cutting away tissue and freeing the lead. This issue, sometimes referred to as "snowplowing," causes the lead to become further stuck in the tissue potentially leading to significant damage to the vasculature or other region of the body and making removal even more difficult. In various embodiments, the system described herein can be utilized to identify when snowplowing is occurring by monitoring the impedance encountered by the system while in operation. Either a sharp increase in impedance over a short time period (e.g., from 300 ohms to 1500 ohms) or a gradual increase to a higher than expected impedance (e.g., over 3000 ohms) may be indicative of snowplowing. In some embodiments, the system can be configured to automatically provide an alert or warning to a user when potential snowplowing is detected. An alert or warning can be provided when a rate of change of impedance exceeds a threshold, when the detected impedance exceeds a threshold value, or both. The alert or warning can be auditory, visual, or both and could be provided by the electrosurgical unit or a separate monitoring/display device. In some embodiments, a plurality of lead removal devices having electrodes of varying diameters can be provided, such that when snow plowing is detected with one lead removal device, a second device having a larger diameter more likely to fit over the lead can be employed.

Example 1

Figure 7A:
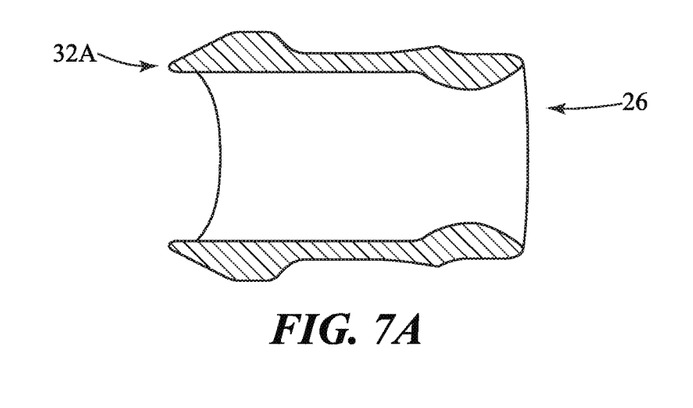
FIGS. 7A-7C depict an exemplary embodiment of a coating and removal process for an electrode tip according to an embodiment of the present disclosure.
Figure 7B:
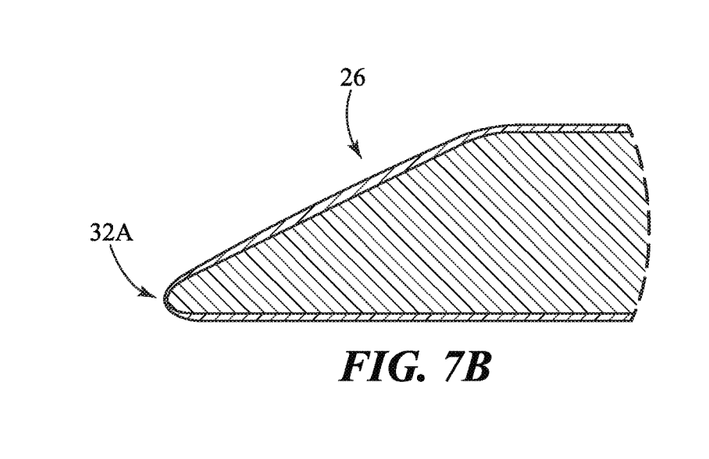
Figure 7C:
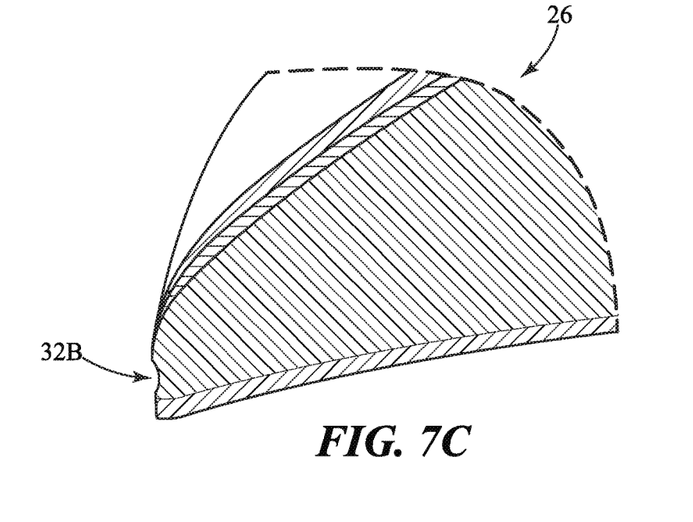

Electrodes from lead extraction devices such as those described above were removed and compared for both activated (n=3) and non-activated (n=3) devices. The electrodes 26 were potted and sectioned for analysis via digital microscopy. By matching the CTE of the metal electrode with the CTE of the dielectric coating, the propensity of the coating to degrade or breakdown after exposure to high temperatures during use is reduced. As such, various metals and various coatings could be used. To activate the devices, a pure CUT duty cycle 20 W waveform was applied for 5 seconds. Post activation, the ceramic coating on the distal cutting edge 32B of the activated electrodes was shown to be completely removed from the circumference of the cutting edge 32B, as shown in FIG. 7C. Measuring from the inner diameter of the cylindrical electrode. This correlates to an average active cutting surface area of about 0.0024 square inches.

Example 2

Lead extraction devices as described herein were used to remove leads from live sheep and were found to successfully cut away tissue and remove leads without harming the sheep. Leads were first pulled by hand using a force gauge to verify that the leads contained tissue ingrowth and were adhered in place. Force gauge readings demonstrated that the leads could not be removed with 3 kilogram-force (6.61 pound-force). Both vascular and sub-sternal leads were removed. Successful lead extraction was accomplished with a low impedance power curve with monopolar Transcollation® at 50 W. Impedance around the electrode during successful extraction was in a range of 70 ohms to 200 ohms. Pure cut (at 50 W), blend (at 50 W), 5% coagulation, 10% coagulation, and monopolar Transcollation® (at 90 W) waveforms were all further tested without harm to the sheep. Histological analysis of the sheep post mortem showed that the lead extraction tool did not cause noteworthy vascular injury as evidenced by the lack of significant hemorrhage or hematoma formation around the vasculature. The intravascular/intima surface is challenging to evaluate grossly for the presence of tool-induced intimal lesions as the tissue sheaths around the leads blended in with the intima/vessel wall. In most cases, there was no evidence of lead extraction tool induced injury inside the heart. In one case the heart had only a small focus of acute myocardial injury due to the lead extraction of the vascular leads. The small myocardial injury would be inconsequential for the heart function.

Although specific and in some cases preferred embodiments have been illustrated and described, it will be appreciated by those of ordinary skill in the art that a variety of alternate or equivalent embodiments calculated to achieve the same purposes may be substituted for the specific embodiments shown and described above. This application is intended to cover any such adaptations or variations of the embodiments discussed herein. Therefore, it is manifestly intended that this invention be limited only by the claims and the equivalents thereof.

What is claimed is:

1. A medical lead extraction system, comprising:
   a hollow flexible elongate catheter;
   a handle attached to a proximal end of the catheter;
   a hollow electrode attached to a distal end of the catheter, the hollow electrode having a body and a distal cutting edge and configured to be advanced over a cardiac lead disposed within a blood vessel of a patient;
   a conductor extending along the catheter and attached to the hollow electrode, the conductor configured to transmit monopolar electrical energy from a radiofrequency power source to the hollow electrode;
   a return electrode defining a monopolar radiofrequency system; and
   an electrically insulating coating surrounding the body of the hollow electrode such that the distal cutting edge of the hollow electrode is exposed to focus the monopolar electrical energy at the distal cutting edge to aid in dissecting tissue to remove the cardiac lead when the distal cutting edge is immersed in fluid in the blood vessel,
   wherein the hollow electrode includes a first portion having a first outer diameter and a second portion having a second outer diameter smaller than the first outer diameter, and wherein the second portion of the electrode is retained within the catheter and the first portion of the electrode extends distally from the catheter, and wherein an outer circumferential wall of the first portion of the electrode has a decreasing radius of curvature towards the distal cutting edge.

2. The medical lead extraction system of claim 1, wherein the electrically insulating coating is configured to initially cover the distal cutting edge of the hollow electrode and degrade from and expose the distal cutting edge when the electrical energy is transmitted to the hollow electrode via the conductor.

3. The medical lead extraction system of claim 1, wherein the electrically insulating coating comprises an enamel coating.

4. The medical lead extraction system of claim 3, wherein a coefficient of thermal expansion of the enamel coating is equal to a coefficient of thermal expansion of a metallic material forming the hollow electrode.

5. The medical lead extraction system of claim 1, wherein an edge radius of the hollow electrode is less than 0.005 inches at the distal cutting edge.

6. The medical lead extraction system of claim 1, wherein the distal cutting edge is sharpened to facilitate mechanical cutting.

7. The medical lead extraction system of claim 1, further comprising an energy source configured to provide monopolar radiofrequency energy to the hollow electrode via the conductor.

8. The medical lead extraction system of claim 1, wherein the electrode is configured to generate plasma at the distal cutting edge when submersed in the blood vessel at operating temperatures of the electrode between 500 degrees Celsius and 800 degrees Celsius.

9. The medical lead extraction system of claim 1 wherein the conductor is attached to the hollow electrode at the second portion of the hollow electrode within the catheter to provide a liquid-tight, insulated connection between the conductor and the hollow electrode.

10. The medical lead extraction system of claim 1, wherein a width of a circumferential wall of the first portion tapers in width towards the distal cutting edge.

11. The medical lead extraction system of claim 1, further comprising a barb projecting outwardly from and extending circumferentially around the hollow electrode, wherein the barb is configured to engage an interior of the hollow flexible elongate catheter to hold the hollow electrode on the hollow flexible elongate catheter, and wherein the barb is formed of a conductive material and the conductor is attached to the hollow electrode at the barb.

12. A medical lead extraction system comprising a hollow electrode extending distally from a hollow flexible elongate catheter, a conductor extending along the catheter and attached to the hollow electrode to transmit monopolar electrical energy from a radiofrequency power source to the hollow electrode, and a return electrode defining a monopolar radiofrequency system, the hollow electrode including a body surrounded by an electrically insulative coating to focus the monopolar electrical energy at an exposed distal cutting edge to aid in dissecting tissue to remove a cardiac lead from a blood vessel when the exposed distal cutting edge is immersed in fluid in the blood vessel, wherein the hollow electrode includes a first portion having a first outer diameter and a second portion having a second outer diameter smaller than the first outer diameter, and wherein the second portion of the electrode is retained within the catheter and the first portion of the electrode extends distally from the catheter, and wherein an outer circumferential wall of the first portion of the electrode has a decreasing radius of curvature towards the distal cutting edge.

13. The medical lead extraction system of claim 12, wherein the electrically insulating coating is configured to initially cover the distal cutting edge of the hollow electrode and degrade from and expose the distal cutting edge when electrical energy is transmitted to the hollow electrode.

14. The medical lead extraction system of claim 12, wherein the electrically insulating coating comprises an enamel coating.

15. The medical lead extraction system of claim 14, wherein a coefficient of thermal expansion of the enamel coating is equal to a coefficient of thermal expansion of a metallic material forming the hollow electrode.

16. The medical lead extraction system of claim 12, wherein an edge radius of the hollow electrode is less than 0.005 inches at the distal cutting edge.

17. The medical lead extraction system of claim 12, further comprising a barb projecting outwardly from and extending circumferentially around the hollow electrode, wherein the barb is configured to engage an interior of the hollow flexible elongate catheter to hold the hollow electrode on the hollow flexible elongate catheter, and wherein the barb is formed of a conductive material and the conductor is attached to the hollow electrode at the barb.

18. The medical lead extraction system of claim 12, wherein the conductor is attached to the hollow electrode at the second portion of the hollow electrode within the catheter to provide a liquid-tight, insulated connection between the conductor and the hollow electrode.

19. The medical lead extraction system of claim 12, wherein a width of a circumferential wall of the first portion tapers in width towards the distal cutting edge.

\* \* \* \* \*